United States Patent [19]

Carlier et al.

[11] Patent Number: 4,971,969
[45] Date of Patent: Nov. 20, 1990

[54] PHARMACEUTICAL COMPOSITION CONTAINING 1-(MONO- OR BIS(TRIFLUOROMETHYL)-2-PYRIDINYL)-PIPERAZINES

[75] Inventors: Patrick Carlier; André Monteil, both of Chatel-Guyon; Claude Poisson, Riom, all of France

[73] Assignee: Akzo N.V., Arnhem, Netherlands

[21] Appl. No.: 439,964

[22] Filed: Nov. 21, 1989

[30] Foreign Application Priority Data

Nov. 24, 1988 [EP] European Pat. Off. ....... 88.402965.3

[51] Int. Cl.$^5$ .................. A61K 31/495; C07D 401/04
[52] U.S. Cl. ...................................... 514/252; 544/360
[58] Field of Search .......................... 544/360; 514/252

[56] References Cited

U.S. PATENT DOCUMENTS 4,876,256 10/1989 Coss et al. ........................... 544/360

FOREIGN PATENT DOCUMENTS 177392 4/1986 European Pat. Off. ............ 544/360

OTHER PUBLICATIONS

Saari et al., J. Med. Chem. 1983, 26, 1696–1701.

Abou-Gharbia, Chem. Abst. 107-217647d, eq. EP 220873 cited in the specification.
Lavielle et al., Chem. Abst 110-75296z (1989) eq. EP 282390 cited in the specification.

Primary Examiner—Cecilia Shen
Attorney, Agent, or Firm—William M. Blackstone

[57] ABSTRACT

Pharmaceutical composition which is useful as a medicinal product, in particular for the treatment of disorders of the central nervous system, characterized in that it contains customary pharmaceutical excipients, and at least one of the compounds of formula

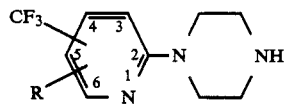

in which the trifluoromethyl substituent is at the 4-position, at the 5-position, or at 4- and 5-positions of the pyridinyl ring, and the substituent R denotes either hydrogen or a halogen, such as chlorine, at position(s) of the pyridinyl ring not occupied by $CF_3$, and its pharmaceutically acceptable salts.

6 Claims, No Drawings

PHARMACEUTICAL COMPOSITION CONTAINING 1-(MONO- OR BIS(TRIFLUOROMETHYL)-2-PYRIDINYL)PIPERAZINES

The present invention relates to a pharmaceutical composition containing 1-[mono- or bis(trifluoromethyl)-2-pyridinyl]piperazines which is useful as a medicament, to new chemical compounds, and to the use of compounds for the preparation of a medicament which act on the central nervous system, in particular as antidepressants, and against obsessive compulsive disorders, anxiety disorders, among which generalized anxiety, panic attacks and agorafobia, obesity, aggression and alcohol addiction.

Such compounds correspond, more precisely, to the following general formula

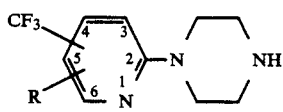
(I)

in which the trifluoromethyl substituent is at the 4-position, at the 5-position, or at 4- and 5-positions of the pyridinyl ring, and the substituent R denotes either hydrogen or a halogen substituent, such as chlorine, at position(s) of the pyridinyl ring not occupied by $CF_3$.

The invention also relates to pharmaceutical compositions containing pharmaceutically acceptable addition salts of the said compounds. These salts are usually obtained by combining the free base (I) with inorganic or organic acids such as hydrochloric, fumaric, maleic, citric or succinic acid, these acids being mentioned only by way of illustration and without implied limitation.

In the prior art, several pyridinylpiperazines containing one or two substituents on the pyridine ring are already known. There may be mentioned, for example, the publication by Walfred S. Saari which appeared in J. Med. Chem. 26 (12), 1696–1701, (1983). 1-(4-trifluoromethyl-2-pyridinyl)piperazine and 1-(5-trifluoromethyl-2-pyridinyl)piperazine, described in Ep 282,390 and Ep 220,873 respectively, are known chemical intermediates, albeit without any pharmaceutical utility. The subject of the invention is a pharmaceutical composition containing pyridinylpiperazines necessarily containing one or two trifluoromethyl substituents at the 4- and/or 5-positions of the pyridinyl ring which is useful as a medicament with activity for the treatment of disorders of the central nervous system. Such medicaments preferably contain 1-(4-trifluoromethyl-2-pyridinyl)piperazine or 1(5-trifluoromethyl-2-pyridinyl)piperazine.

The compounds of formula I in which the trifluoromethyl substituent is at the 4-position, at the 5-position, or at 4- and 5-positions of the pyridinyl ring, and the substituent R denotes either hydrogen or a halogen substituent at position(s) of the pyridinyl ring not occupied by $CF_3$, and their pharmaceutically acceptable salts, with the proviso that R denotes a halogen when only one trifluoromethyl substituent is present, are new.

The compounds with formula I possess specific antidepressant activity, resulting especially from their 5HT1B type serotoninergic agonist properties, and are prepared according to known processes for similar compounds.

According to one embodiment, an excess of piperazine is reacted with a suitably substituted 2-halopyridine in an organic solvent, heating to reflux of the solvent. Acetonitrile can be taken, for example, as a suitable solvent. This process corresponds to the following scheme:

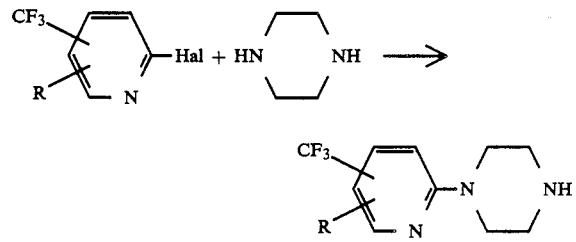

Hal denotes a halogen such as chlorine.

According to another embodiment, a suitably substituted 2-halopyridine is reacted in an organic solvent in the presence of a base with a piperazine in which one of the

groups is protected by a group R', and the protective group is then removed in the usual manner such as by hydrolysis or hydrogenation. By using an alcohol such as butanol as the organic solvent, the base may be a carbonate or a tertiary amine such as triethylamine. As a protective group R', the following will be used, for example:

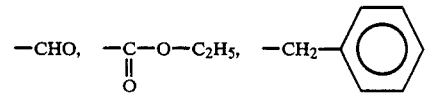

This process corresponds to the f©ll©wing scheme:

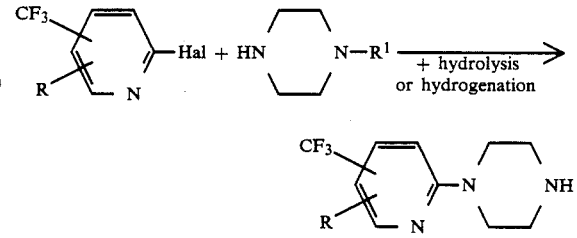

Hal denotes a halogen such as chlorine.

The compounds of the invention and the processes for producing them are described in the examples below, without this constituting a limitation to the different embodiments.

EXAMPLE 1:

1-(3-chloro-5-trifluoromethyl-2-pyridinyl)piperazine

A solution of 10.8 g (0.05 mol) of 2,3-dichloro-5-trifluoromethylpyridine and 12.9 g (0.15 mol) of anhydrous piperazine in 100 ml of acetonitrile was introduced into a reactor, and the mixture was then heated under reflux for 2 hours. After the mixture was cooled, the precipitate was filtered off and washed with acetonitrile and the filtrate was then evaporated. The residue was then taken up with chloroform and washed with water. After the organic phase was dried and the solvent then evaporated off, the residue was distilled and the product of the title was obtained in the form of a base having a boiling point B.p. $_{0.06}$ of 101° C.

To obtain the hydrochloride, the base obtained was treated with an ethanol/hydrochloric acid mixture, and the precipitate obtained was then washed with ether and dried.

5.5 g of the compound of the title were thereby obtained in the form of a hydrochloride having a melting point M.p. of 178° C.

EXAMPLE 2:

1-[4,5-bis(trifluoromethyl)-2-pyridinyl]piperazine

Working as described in Example 1, but starting with 10 g (0.04 mol) of 2-chloro-4,5-bis(trifluoromethyl)pyridine and 10.3 g (0.12 mol) of piperazine, the base having a boiling point B.p. $_{0.04}$ of 100-102° C. was obtained, and then, after conversion to the hydrochloride, 7.8 g of the title compound.

EXAMPLE 3:

1-(5-trifluoromethyl-2-pyridinyl)piperazine

Working as described in Example 1, but starting with 2-chloro-5-trifluoromethylpyridine, 10.4 g of the title compound were obtained in the form of a base having a boiling point B.p. $_{0.05}$ of 91° C.

The dihydrochloride obtained according to the usual methods has a melting point M.p. of 262° C.

According to the same process, the compounds whose characteristics are given in Table I below were also obtained.

TABLE I

| COMPOUND NO. | | | Base B.p. °C. (mm Hg) | Hydrochloride M.p. °C. |
|---|---|---|---|---|
| 1 (Example 3) | 5 CF$_3$ | | 91° (0.05 mm) | 262° C. |
| 2 | 4 CF$_3$ | | 114–115° (0.35 mm) | 224° C. |
| 3 | 5 CF$_3$ | 6 Cl | 118° (0.06 mm) | Decomposition |
| 4 (Example 2) | 4 CF$_3$ | 5 CF$_3$ | 100° (0.04 mm) | Decomposition |
| 5 (Example 1) | 5 CF$_3$ | 3 Cl | 101° (0.06 mm) | 178° C. |

The activity of the compounds of the invention on the central nervous system was demonstrated by the pharmacological tests below, demonstrating the serotoninergic activity and specifying the mode of action.

BINDING TEST

This test is carried out according to the protocol of PEROUTKA, S.J. ["Selective labelling of 5-HT1A and 5HT1B binding sites in bovine brain" BRAIN RESEARCH 344, p. 167–171 (1985)]. In this test, the affinity for 5HT1A receptors is determined by the Capacity of the compounds to displace [$^3$H]-8-OH-DPAT from the membranes of the rat hippocampus; similarly, the affinity for 5HT1B receptors is determined by the capacity of the compounds to displace [$^3$H]-5HT from the membranes of the rat striatum.

The results recorded in Table II below show the pKi values calculated according to the abovementioned protocol.

PENILE ERECTION TEST

This test, carried out according to the protocol of BERENDSEN H.H.G. and BROEKKAMP C.L.E. ["Drug induced penile erections in rats: indication of serotonin 1B receptor mediation—EUROPEAN J. PHARMACOL. 135, 279-287 (1987")]enables the 5HT1B agonist potentials of the various compounds to be assessed.

The results recorded in Table II below show the minimum dose in mg.kg$^{-1}$ administered subcutaneously which leads to an erection of the penis in rats, as well as the activity when administered orally.

TABLE II

| COMPOUND NO. | BINDING pKi | | ERECTION OF THE PENIS |
|---|---|---|---|
| | 5HT1A | 5HT1B | |
| 1 | <5.0 | 6.3 | 1 (>46 PO) |
| 2 | 5.6 | 6.9 | 1 (2.2 PO) |
| 3 | 5.6 | 7.0 | 0.46 (4.6 PO) |
| 4 | 4.1 | 6.4 | 10 (2.2 PO) |
| 5 | 5.4 | 6.3 | 4.6 (10 PO) |

These results show that the compounds of the invention possess overall a greater affinity for 5HT1B receptors than for 5HT1A receptors.

Moreover, the toxicity of the compounds of the invention appears to be low: at an oral dose of 160 mg.kg$^{-1}$, no mortality is observed in mice.

These collective pharmacological properties hence enable the compounds of the invention to be applied in human therapy as a medicinal product for the treatment of disorders of the central nervous system, in particular as antidepressants.

In combination with customary pharmaceutical excipients, the compounds of the invention may be administered at daily doses of between 0.1 mg and 5 mg per kg of body weight. In human therapy, daily doses of between 10 mg and 150 mg, administered orally, will preferably be used.

The compounds according to the invention can be processed to pharmaceutical preparations for enteral administration, local application or parenteral administration by mixing with suitable auxiliaries. A suitable form for administration is a tablet, pill, powder, capsule, paste, spray, sirup, ointment, suppository, solution, suspension or emulsion. For instance, the following pharmaceutical dosage forms were prepared:

| Tablet | |
|---|---|
| 1-(5-trifluoromethyl-2-pyridinyl)piperazine dihydrochloride | 50 mg |
| hydroxypropyl cellulose (HPC) | 7,5 mg |
| corn starch | 25 mg |
| magnesium stearate | 1,25 mg |
| aerosil | 2,5 mg |
| lactose | to 250 mg |

The active principle, lactose and corn starch were mixed. An aquous HPC solution was added and the mass was granulated in several minutes. The resulting mass was dried, sieved and aerosil and magnesium stearate were added. After mixing the mass was compressed to form tablets each weighting 250 mg.

| Injectable preparation | |
|---|---|
| 1-(4-trifluoromethyl-2-pyridinyl)piperazine | 15 mg |
| NaOH/HCl | to pH 5 |
| mannitol | to isotonic |
| water for injections | to 1 ml |
| dissolve the components, adjust to volume and pH. | |

Freeze-dried injectable preparations

The same components as for the injectable preparation were dissolved and adjusted to pH 5, and the solution was freeze-dried.

| Capsule | |
|---|---|
| active component | 50 mg |
| HPC | 3 mg |
| corn starch | 15 mg |
| magnesium stearate | 1,5 mg |
| lactose | to 150 mg |
| The components were processed as for the tablet and the resulting mass was filled into capsules. | |
| Suppository | |
| compound of example 1 | 5 mg |
| whitepsol 558 | 500 mg |
| The wax was melted and the active compound was dissolved therein. | |

We claim:

1. Pharmaceutical composition that is useful as a medicinal product comprising customary pharmaceutical excipients and an effective amount for treating disorders of the central nervous system by 5HT1B type serotoninergic agonist activity of at least one compound of formula

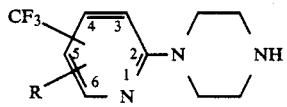

in which a trifluoromethyl substituent is at the 4-position, at the 5-position, or at 4- and 5-positions of the pyridinyl ring, and the substituent R denotes either hydrogen or halogen substituent at positions of the pyridinyl ring not occupied by CF₃, or a pharmaceutically acceptable salt thereof.

2. Pharmaceutical composition according to claim 1, comprising 1-(5-tri-fluoromethyl-2-pyridinyl piperazine or a pharmaceutically acceptable salt thereof.

3. Pharmaceutical composition according to claim 1, comprising 1-(4-tri-fluoromethyl-2-pyridinyl piperazine or a pharmaceutically acceptable salt thereof.

4. A compound or a pharmaceutically acceptable salt thereof of the formula

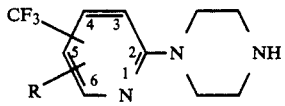

in which a trifluoromethyl substituent is at the 4-position, at the 5-position, or 4- and 5-positions of the pyridinyl ring, an the substituent R denotes either hydrogen or a halogen substituent at positions of the pyridinyl ring not occupied by CF₃, and their pharmaceutically acceptable salts, with the proviso that R denotes a halogen when only one trifluoromethyl substituent is present.

5. Compound according to claim 4, selected from the group consisting of 1-(3-chloro-5-trifluoromethyl-2-pyridinyl)-piperazine, 1-(4,5-bis(tri-fluoromethyl)-2-pyridinyl)-piperazine, and 1-(5-trifluoromethyl-6-chloro-2-pyridinyl)-piperazine, or a pharmaceutically acceptable salt thereof.

6. Method for treating disorders of the central nervous system through 5HT1B type serotoninergic agonist activity comprising administering pharmaceutically effective amounts of at least one compound of the formula

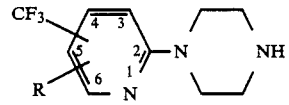

in which a trifluoromethyl substituent is at the 4-position, at the 5-position, or at 4- and 5-positions of the pyridinyl ring, and the substituent R denotes either hydrogen or a halogen substituent at positions of the pyridinyl ring not occupied by CF₃, or a pharmaceutically acceptable salt thereof.

* * * * *